US00PP25296P3

(12) United States Plant Patent
Olesen

(10) Patent No.: US PP25,296 P3
(45) Date of Patent: Feb. 24, 2015

(54) MINIATURE ROSE PLANT NAMED 'POULTY011'

(50) Latin Name: ***Rosa* hybrid**
Varietal Denomination: Poulty011

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 143 days.

(21) Appl. No.: 13/507,032

(22) Filed: May 31, 2012

(65) Prior Publication Data

US 2013/0326752 P1 Dec. 5, 2013

(51) Int. Cl.
*A01H 5/00* (2006.01)

(52) U.S. Cl.
USPC ..... Plt./122

(58) Field of Classification Search
CPC ..... A01H 5/0222; A01H 5/00; A01H 5/0831
USPC ..... Plt./122, 129, 150
See application file for complete search history.

(56) References Cited

PUBLICATIONS

Mai. Rose Propagation for Home Gardeners, revised 2008, pp. 1-43.*
Taklo. Virtuel make-over of floradania.dk, Gartner tidende Nr. 2, torsday, Jan. 22, 2009, 125 argang, pp. 1-3 and 32-36.*

* cited by examiner

*Primary Examiner* — June Hwu

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty011'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2005 and the resulting seeds were planted in a controlled environment in Fredensborg, Denmark. The new variety, named 'Poulty011', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant red flowers;
2. Vigorous and compact growth;
3. Year-round flowering under heated and unheated glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulty011' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty011' was selected by the inventor as a single plant from the progeny of the hybridization in 2005.

Asexual reproduction of 'Poulty011' by cuttings was first done by Mogens N. Olesen in the nursery in Fredensborg, Denmark in 2006. This initial and other subsequent propagations conducted in controlled environments have demonstrated that the characteristics of 'Poulty011' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty011'. Specifically illustrated in the drawing are flowers at various stages of development, flower in parts, leaves, and stems.

DETAILED DESCRIPTION OF THE VARIETY

The following is a description of 'Poulty011', as observed in its growth in glasshouses in Burlington, Ontario Canada. Observed plants are 2 months of age and were cultivated in 10.5 cm pots. Color references are made using The Royal Horticultural Society (London, England) Colour Chart, 2001, except where common terms of color are used.

For a comparison, several physical characteristics of the rose variety 'Poulpar029', U.S. Plant Pat. No. 16,148. are compared to 'Poulty011' in Chart 1.

CHART 1

| | 'Poulty011' | 'Poulpar029' |
|---|---|---|
| Petalage: | 30 petals | 30 petals |
| Flower Diameter: | 35 to 40 mm | 35 mm |
| General Tonality of Flower Color: | Red Group 45B | Red Group 53A |

FLOWER AND FLOWER BUD

Blooming habit: Continuous.

Flower bud:

*Size*.—Upon opening, 20 mm in length from base of receptacle to end of bud. 10 mm in diameter.

*Bud form*.—Ovate.

*Bud color*.—As sepals unfold, petals are Red Group 53A.

*Sepals*.—Upper Surface: Color: Green Group 143C. Texture: Smooth, weak pubescence. Lower Surface: Color: Yellow Green Group 144A. Texture: Smooth. Shape: Apex: Cirrhose. Base: Flat at union with receptacle. Margins: Margins have moderate foliaceous appendages on three of the five sepals. Size: 25 mm long by 5 mm wide.

*Receptacle*.—Surface Texture: Smooth. Shape: Campanulate. Size: 5 mm tall and 4 mm wide. Color: Yellow Green Group 144A.

*Pedicel*.—Surface: Smooth. Few stipitate glands. Length: 15 mm on average. Diameter: Generally 2 mm. Color: Yellow-Green Group 144A. Strength: Medium strength.

*Borne*.—1 to 3 flowers per branch.

Flower bloom:

*Fragrance*.—None.

*Duration*.—Flowers last up to 28 days on the plant.

*Size*.—Open flowers diameter is 35 to 40 mm. Flower depth is 15 mm.

*Form*.—General shape is a hybrid tea with a high pointed center upon opening. Fully mature flowers resemble an open cup with petals curving outward from the center.

*Shape of flower, side view*.—The upper portion is flat. The lower portion is a flattened convex.

Petalage: Under normal conditions, flowers have 30 petals total, 5 of which are petaloids.

Color:

*General tonality*.—On open flower Red Group 45B. Coloration does not change.

*Upon opening*.—Inner and outer petals are Red Group 45B on the upper surface. Red Group 53C on the lower surface. At the base of the petal on upper and lower surface, there is a small white spot White Group 155B.

*After opening*.—Inner and outer petals are Red Group 45B on the upper surface. Red Group 53C on the lower surface. At the base of the petal on upper and lower surface, there is a small white spot White Group 155B. Occasional white streaks on the undersurface of the petal White Group 155B.

Petals:

*Petal reflex*.—Moderate.

*Margin*.—Entire, uniform, no undulations in the margin.

*Shape*.—Generally narrow and elliptic. Apex shape: Rounded. Base shape: Acute.

*Size*.—20 mm (l) by 19 mm (w).

*Texture*.—Smooth.

*Thickness*.—Average.

Petaloids:

*Quantity*.—5 on average.

*Shape*.—Irregular, and asymmetric. The apex is rounded, and the base is acute.

*Color*.—Red Group 45B on the upper surface. Red Group 53C on the lower surface. At the base of the petaloid on upper and lower surface, there is a small white spot.

*Size*.—12 mm (l) by 9 mm (w).

Reproductive organs:

*Pollen*.—None Observed.

*Anthers*.—Size: 2 mm long. Color: Greyed-Orange Group 163B. Quantity: 35 on average.

*Filaments*.—Color: Yellow Group 4A. Length: About 2 to 3 mm.

*Pistils*.—Length: About 3 mm long. Quantity: 25 on average.

*Stigmas*.—Level relative to the length of the filaments and the height of the anthers. Color: Greyed-Yellow Group 162A.

*Styles*.—Color: Greyed-Red Group 180B.

*Seed formation*.—Not observed.

PLANT

Plant growth: Upright to bushy. Plants are about 15 cm in height, and 15 cm wide.

Stems:

*Color*.—Juvenile growth: Yellow-Green Group 144A. Mature growth: Yellow-Green Group 146B.

*Length*.—Canes are about 10 cm from the base of the plant to the flowering portion.

*Diameter*.—3 mm on average.

*Internodes*.—On mature canes, there is an average distance of 20 mm between nodes.

*Surface texture*.—Young and mature wood is smooth.

Prickles:

*Incidence*.—7 per 10 cm of stem.

*Size*.—Average length 3 mm.

*Color*.—Juvenile prickles are Greyed-Orange Group 173C. Mature prickles are Greyed-Red Group 180B.

*Shape*.—Upper side is linear, lower is concave.

Plant foliage:

*Compound leaf size*.—65 mm (l) by 40 mm (w).

*Quantity*.—4 leaves per 10 cm of stem.

*Leaf bearing angle to stem*.—60 degrees.

*Color of juvenile foliage*.—Upper Leaf Surface: Yellow-Green Group 146B. Lower Leaf Surface: Yellow-Green Group 146B. Margins: Greyed-Red Group 181A.

*Color of mature foliage*.—Upper Leaf Surface: Yellow-Green Group 147A. Lower Leaf Surface: Yellow-Green Group 147B.

Plant leaves and leaflets:

*Stipules*.—Size: About 6 mm in length. Shape: Linear, slightly broad based with outward extending apecies. Margins: Finely serrated with few stipitate glands. Color: Yellow-Green Group 144A.

*Petiole*.—Length: 20 mm on average. Diameter: About 1 to 2 mm. Upper surface: Yellow-Green Group 146B with anthocyanic intonations the color of Greyed-Purple Group 183B. Smooth. Lower surface: Yellow-Green Group 144A. Smooth.

*Rachis*.—Length: 25 mm on average. Diameter: About 2 mm. Upper surface: Yellow-Green Group 146B with anthocyanic intonations the color of Greyed-Purple Group 183B. Smooth. Lower surface: Yellow-Green Group 144A. Smooth.

*Leaflet*.—Number of leaflets: 5 on normal leaves in middle of the stem. Size: About 28 mm in length by 18 mm wide. Margin: Serrate. General Shape: Elliptical. Apex Shape: Acute. Base Shape: Round. Texture: Smooth upper and undersurface. Arrangement: Odd pinnate. Venation: Reticulate. Leaf Gloss: Somewhat glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Above average resistance to powdery mildew *Sphaerotheca pannosa*, downy mildew *Peronospora sparsa*, rust *Phragmidium* spp., black spot *Diplocarpon rosae*, and *Botryis cinerea* under normal growing conditions.

The invention claimed is:

1. A new and distinct variety of rose plant of the miniature class named 'Poulty011', substantially as illustrated and described herein, due to its abundant, red flowers, vigorous growth, compact habit, suitability for production from softwood cuttings in pots, and durable flowers and foliage that make the variety suitable for distribution in the floral industry.

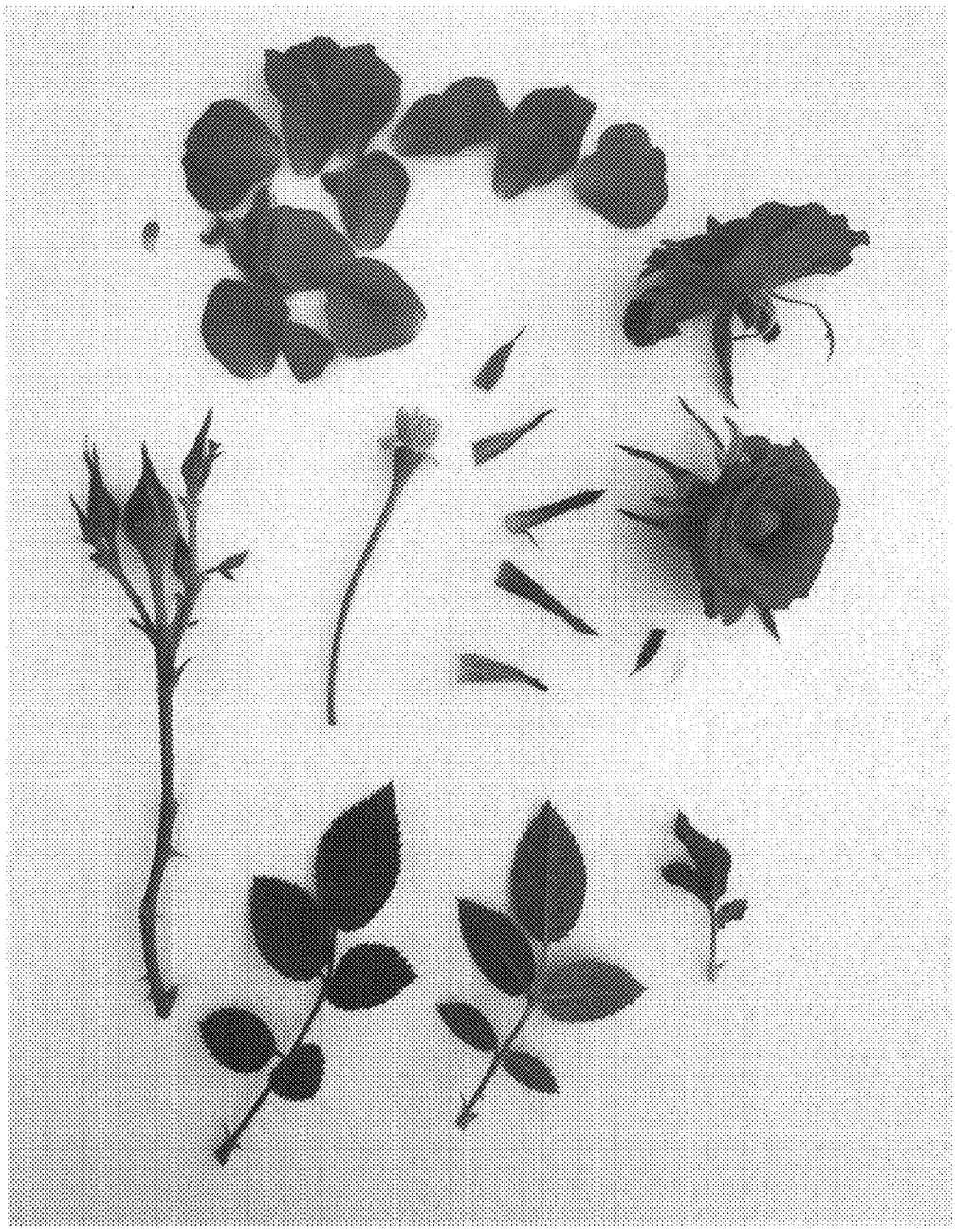

* * * * *